(12) United States Patent
Visser et al.

(10) Patent No.: US 9,408,804 B2
(45) Date of Patent: Aug. 9, 2016

(54) METHOD FOR KEEPING AN IMMUNOGENIC COMPOSITION AVAILABLE FOR ADMINISTRATION TO AN ANIMAL

(75) Inventors: Nicolaas Visser, Boxmeer (NL); Theodorus Jansen, Boxmeer (NL)

(73) Assignee: Intervet Inc., Madison, NJ (US)

( * ) Notice: Subject to any disclaimer, the term of this patent is extended or adjusted under 35 U.S.C. 154(b) by 11 days.

(21) Appl. No.: 13/320,857

(22) PCT Filed: May 18, 2010

(86) PCT No.: PCT/EP2010/056815
§ 371 (c)(1),
(2), (4) Date: Dec. 15, 2011

(87) PCT Pub. No.: WO2010/133592
PCT Pub. Date: Nov. 25, 2010

(65) Prior Publication Data
US 2012/0087945 A1    Apr. 12, 2012

Related U.S. Application Data

(60) Provisional application No. 61/179,548, filed on May 19, 2009.

(30) Foreign Application Priority Data

May 18, 2009  (EP) ..................... 09160451

(51) Int. Cl.
| | | |
|---|---|---|
| *A61K 39/135* | (2006.01) | |
| *A61K 9/113* | (2006.01) | |
| *A61K 47/06* | (2006.01) | |
| *A61K 9/107* | (2006.01) | |
| *A61K 39/39* | (2006.01) | |
| *A61K 47/26* | (2006.01) | |
| *A61K 39/12* | (2006.01) | |
| *A61K 39/00* | (2006.01) | |

(52) U.S. Cl.
CPC ............... *A61K 9/107* (2013.01); *A61K 39/12* (2013.01); *A61K 39/135* (2013.01); *A61K 39/39* (2013.01); *A61K 47/06* (2013.01); *A61K 47/26* (2013.01); *A61K 9/113* (2013.01); *A61K 2039/552* (2013.01); *A61K 2039/55566* (2013.01); *C12N 2770/32134* (2013.01)

(58) Field of Classification Search
CPC ................... A61K 2039/55566; A61K 39/135; A61K 9/107; A61K 8/062; A61K 8/064; A61K 2039/552
See application file for complete search history.

(56) References Cited

U.S. PATENT DOCUMENTS 7,998,488 B2 *  8/2011  Oberreither et al. ........ 424/199.1

FOREIGN PATENT DOCUMENTS

| EP | 1 201 251 A1 | 5/2002 |
| WO | WO 01/45670 A2 | 6/2001 |

OTHER PUBLICATIONS

Garland A.J.M. (Vaccine 1999, vol. 17 (13-14), pp. 1760-1766).*
Barnett et al. (A) Vaccine 1996, vol. 14, No. 13, pp. 1187-1198.*
Barnett et al. (B) Vaccine, 2002, vol. 20, pp. 2060-2064.*
Filgueira et al. Vaccine 1995, vol. 13, No. 10, pp. 953-960.*
Sadir et al. Veterinary Immunolgy and Immunopathology 1999, vol. 69, pp. 11-22.*
Wikipedia, the free encyclopedia, published on Jun. 25, 2015.*
Barnett et al., "Stratified and cryogenically stored (SACS) vaccines, a new concept in emergency foot-and-mouth disease vaccine formulation and storage", Vaccine, (2002), pp. 2060-2064, vol. 20(16).
International Search Report corresponding to PCT/EP2010/056815, mailed Jul. 29, 2010.

* cited by examiner

*Primary Examiner* — Bao Li

(57) ABSTRACT

The present invention pertains to a method for keeping an immunogenic composition available for administration to an animal, wherein said composition comprises an antigen and an emulsion which is a single emulsion at a first temperature below a body temperature of the animal and which emulsion reverses at a second temperature between the first temperature and the body temperature, said method comprising providing the composition, freezing the composition, and storing the frozen composition until it is needed for administration to the animal. The invention also pertains to a method for testing an immunogenic composition, and an immunogenic composition, optionally in combination with specific instructions for storing the composition.

9 Claims, 5 Drawing Sheets

[Graph titled "Asia 1 Shamir" showing Titer (10log) vs Time (months). Liquid (solid line) decreases from ~1.65 at 0 months to ~1.5 at 4 months to ~1.2 at 12 months. Frozen (dashed line) remains constant at ~1.65.]

METHOD FOR KEEPING AN IMMUNOGENIC COMPOSITION AVAILABLE FOR ADMINISTRATION TO AN ANIMAL

CROSS-REFERENCE TO RELATED APPLICATIONS

This application is a national phase filing under 35 USC 371 of International Application No. PCT/EP2010/056815 filed May 18, 2010, which claims priority to EP 09160451.2 filed May 18, 2009 and U.S. Provisional Application No. 61/179,548 filed May 19, 2009, all of which are relied on for priority and incorporated herein by reference.

FIELD OF THE INVENTION

The present invention pertains to a method for keeping an immunogenic composition available for administration to an animal. The invention also pertains to a method for testing an immunogenic composition, and an immunogenic composition, optionally in combination with specific instructions for storing the composition.

GENERAL BACKGROUND

In medicine immunogenic compositions for administration to animals (including humans) are frequently used. Such a composition may for example be a vaccine or a diagnostic composition. Often such a composition contains an adjuvant to improve the immunological response in the animal. An important class of adjuvants, in particular in veterinairy medicine, are emulsions containing oily substances, for example emulsions of the so-called oil-in-water (O/W), water-in-oil (W/O) or water-in-oil-in-water (W/O/W) type, wherein the oily substance in general serves as the compound to boost the immunological response.

In every day practice it is advantageous that immunogenic compositions have long shelf-lives. This means that they can be stored for a long time while keeping an adequate efficacy, until needed for administration to an animal. It is generally known that antigens per se are best kept at low temperatures. However, in particular emulsions cannot be frozen without detrimental effect on their adjuvanting properties. Freezing namely can be disadvantageous for the quality of the emulsion and hence for the quality of the adjuvanting properties. Therefore, commercially available immunogenic compositions comprising adjuvanting emulsions are always accompanied with the instruction to store the composition above a freezing temperature of the emulsion. In practice, since most adjuvant emulsions are based on water, this means that the compositions are typically stored between 2 and 8° C. Although ideally suitable for maintaining an adequate emulsion quality, a temperature of between 2° C. and 8° C. means that many antigens (which often comprise complex protein or other biopolymer structures) are prone to noticable deterioration. In particular for antigens which are not too stable by nature, such as foot-and-mouth disease antigens, this means that the immunogenic properties can easily fall below an adequate level within 12 months from initial production.

In the prior art this problem has been noticed and several solutions have been found. One of these is to store the antigens separately from the adjuvant emulsion. This way, the antigens can be stored for example at a temperature of −196° C., and the emulsion at 4° C. This way, both constituents can maintain their desired properties for many years. A disadvantage of this method is that it takes some time to formulate the immunogenic composition and distribute them when needed for administration to an animal. Typically this takes 72 to 120 hours. In case of an emergency, this may be too long. Also, when there is such an emergency and the composition has to be delivered immediately after it has been formulated, the safety and potency of the composition cannot be tested.

Another solution is known from EP 1 201 251. In this patent a method is described for obtaining stratified cryogenically stored vaccines (so called SACS). This method is based on an approach of layering the individual components of a vaccine in the same primary container and then storing the product at ultra-low temperatures (around −150° C.). Although with this method a detrimental effect on potency is avoided, the method is very complex and the fact that the vaccine has to be stored at ultra-low temperatures makes the method very expensive to apply.

OBJECT OF THE INVENTION

It is an object of the invention to overcome or at least mitigate prior art problems pertaining to the storage of immunogenic compositions until needed for administration to an animal, and to provide a convenient way of keeping such composition available for use. It is another object of the invention to provide a novel method for testing an immunogenic composition, a novel combination of an immunogenic composition and an instruction for storing the composition, as well as a novel liquid immunogenic composition.

SUMMARY OF THE INVENTION

The first object of the invention is met by providing a method according to the preamble of this description, wherein said composition comprises an antigen and an emulsion which is a single emulsion at a first temperature below a body temperature of the animal and which emulsion reverses at a second temperature between the first temperature and the body temperature (including at a body temperature), said method comprising providing the composition (i.e. making the composition available, for example by formulating it or simply buying it on the market), freezing the composition, and storing the frozen composition until it is needed for administration to the animal.

The second object is met by providing a method for testing an immunogenic composition for administration to an animal, said composition comprising an antigen and an emulsion which is a single emulsion at a first temperature below a body temperature of the animal and which emulsion reverses at a second temperature between the first temperature and the body temperature, said method comprising formulating the immunogenic composition, freezing the composition, storing the frozen composition for a predetermined time, thawing the composition, and determining the potency of the thawed composition.

The third object of the invention is met by providing a combination of an immunogenic composition for administration to an animal, said composition comprising an antigen and an emulsion which is a single emulsion at a first temperature below a body temperature of the animal and which emulsion reverses at a second temperature between the first temperature and the body temperature, and an instruction that the composition may be stored at a temperature below a freezing temperature of this composition until needed for administration to the animal.

The fourth object of the invention is met by providing a liquid immunogenic composition for administration to an animal, the composition comprising an antigen and an emulsion which is a single emulsion at a first temperature below a body temperature of the animal and which emulsion reverses at a second temperature between the first temperature and the body temperature, which composition was frozen around −20° C. and thawed thereafter to become liquid.

DEFINITIONS

Snap-freezing: a process by which the temperature of a sample is very quickly lowered to temperatures below −140° C. by submerging the sample in a liquid having a temperature below −140° C. (in particular liquid nitrogen at −196° C.) or the gaseous phase of such a liquid.

Freezing around −20° C.: to freeze under conditions similar to freezing in a standard house-hold compressor type freezer, having an inner temperature (in the freezing compartment) typically between −12 and −28° C.

Immunogenic composition: a composition that has the capacity to trigger the immune system of a host when the composition is administered to that host.

Potency: a measure of the capacity to trigger the immune system of a host.

Vaccine: a constitution suitable for application to an animal (including humans), comprising one or more antigens (such as attenuated or killed microorganisms and/or subunits thereof, or any other substance such as a metabolite of an organism), in an immunologically effective amount (i.e. capable of stimulating the immune system of the target animal), typically combined with a pharmaceutically acceptable carrier (such as for example a liquid containing water), optionally comprising immunostimulating agents (adjuvants), which upon administration to the animal induces an immune response which suffices to treat a disease or disorder of the animal, i.e. to at least aid in preventing, ameliorating or curing the disease or disorder.

Adjuvant: a substance or composition that is able to favor or amplify a particular process in the cascade of immunological events, ultimately leading to a better immunological response against an antigen.

To ship: to cause to be conveyed to a destination, for example using ordinary mail or express carriage, using road haulage, air transport, transport over water or whatever means suitable for a package or other tangible item.

DESCRIPTION OF THE INVENTION

Surprisingly applicant has found that, against the common knowledge and instructions of suppliers of adjuvant emulsions, one can freeze an immunogenic composition when this is based on an emulsion which is a single emulsion (in essence an emulsion of the O/W or W/O type) at a first temperature below a body temperature of the animal and which emulsion reverses at a second temperature (i.e. at least starts to reverse at this second temperature) between the first temperature and the body temperature. Reversing in this sense means that the phase which is emulsified at the first temperature is urged to become the continuous phase at the second temperature, and at the same time, that the phase which is the continuous at the first temperature is urged to be emulsified in the other phase at the second temperature. Such emulsions are at present commercially used. For example, Intervet/Schering-Plough Animal Health sells a foot-and-mouth disease (FMD) vaccine called DECIVAC® FMD-DOE, which comprises an emulsion which is a (single) oil-in-water emulsion below 25° C. but which reverses at a higher temperature, for example at 37° C. Since this reversion takes place in the body of the animal, no stirring is available and part of the water will remain present as a continuous phase, even after reversion. Therefore, the final reversed water-in-oil emulsion will have some water present as continuous phase even after reversion. The result is thus an emulsion of the water-in-oil type in the presence of some water as apparent continuous phase. Therefore, such an emulsion is often referred to as a double-emulsion (although technically it is not). Although the supplier strictly instructs not to freeze the composition, we have found that freezing hardly (or even not) affects the adjuvanting properties of the emulsion. The reason for this is not totally clear but may be due to the fact that the emulsion has to revert anyway upon administration to an animal. This may mean that the emulsion quality before the reversion takes place is not or less relevant for the emulsion quality afterwards. Thus, although the emulsion quality may decrease significantly upon freezing, this appears to have little or even no effect on the adjuvanting properties of the emulsion after reversion. The advantage of the presently found effect is that the immunogenic composition can be stored at significantly lower temperatures, and thus that the natural deterioration speed of the antigens in the composition can inherently be slowed down (typically by a factor 2 per 10 degrees lower storage temperature for normal chemical reactions; or even a complete blockade for catalysed reactions and enzymatic processes), no matter which antigens are being used. It is noted that the emulsion may contain one ore more surfactants to obtain the reversing properties. However, it may also be that the antigen itself serves to provide these properties since antigens may have surfactant-like properties. In any case, how to obtain a single emulsion that reverses at a certain temperature (i.e. at or above this temperature), is commonly known in the art.

It is noted that based on data produced with frozen FMD vaccine, EP 1 201 251 suggests that snap-freezing an emulsion based vaccine and storing the vaccine in frozen condition might be an option for vaccines having an emulsion formulated with Montanide ISA 206 oil (available from SEPPIC, France), but apparently this option was generally regarded as having no reasonable chance of success given the specific instructions from the manufacturer (SEPPIC) not to store an emulsion based on Montanide ISA 206 in frozen condition. Indeed, applicant of EP 1 201 251 himself has chosen the route of SACS instead of freezing, and no other skilled person explored the route of freezing since the publication of the said EP patent application early 2002, despite the great need for adequately storing unstable immunogenic compositions. Applicant however, despite the clear teaching not to pursue the option of freezing but follow the route of SACS, found that storing an immunogenic composition in frozen condition, at least when using an emulsion as indicated here-above, is a very simple and effective way of keeping the composition available for administration to an animal. In case of an emergency situation, the composition can simply be thawed and administered immediately which is a significant advantage, especially in case of an emergency situation where large amounts of immunogenic composition might need to be available within hours.

In an embodiment a potency of the immunogenic composition is established before it is stored. It is very advantageous when the potency of an immunogenic composition is known before administration. In the prior art, when immunogenic compositions are formulated in case of an emergency situation, there is not time left to assess the potency of the composition. With the present invention, use can be made of a validated composition.

In an embodiment the composition is supplied to a third party (also covering a mailing address that is different from the place of residence of the third party) upon its request, before it is frozen. In this embodiment, the manufacturer does not need to freeze the composition before it is shipped to a third party. The said third party may store the composition itself in frozen condition. This embodiment is particularly advantageous when the third party envisages that large amounts of the composition may need to be available immediately when an emergency situation arises and no time should be lost. Alternatively, the composition is supplied to a third party upon its request after it has been frozen. In this embodiment it may be that the manufacturer of the immunogenic composition is the party that stores the composition in frozen condition. This has the advantage that the manufacturer may have permanent control over the circumstances under which the composition is stored until it is shipped to a third party.

In an embodiment the composition is frozen by using a non snap-freezing process. A snap-freezing process has the important disadvantage that specific, often expensive apparatus is needed. Such apparatus may not be available at each and every location at which a party wants to store the immunogenic composition. Moreover, a snap-freezing process requires trained operators in view of the risks involved when working with liquids at ultra-low temperatures (choking, burning wounds etc). Applicant surprisingly found that in the present invention, one can make use of a non snap-freezing process to freeze the composition. It has been found even that a conventional compressor type freezer, such as an ordinary house-hold type freezer, will suffice. Although the freezing time is significantly longer in such a freezer, and thus the negative impact on emulsion quality may be tremendous, applicant surprisingly found that in the present method this has no or hardly any negative influence on the potency of the immunogenic composition. It has even appeared to be adequate when freezing takes place around −20° C., i.e. at a freezing temperature as present in an ordinary house-hold type freezer.

In an embodiment the composition is stored for more than 4 months, in particular more than 12 months. It has been found that storing for such periods of time does not, or hardly, affect the adjuvanting properties of the emulsion. In an embodiment the single emulsion is an oil-in-water emulsion, preferably an emulsion wherein the oil comprises a mixture of mannide oleate and mineral oil. Such an emulsion has proven to be ideally suitable in the present invention. In particular, the present invention is suitable for an immunogenic composition containing a foot-and-mouth disease (FMD) antigen. It is commonly known that FMD antigens are inherently instable, and are best preserved at very low temperatures. The present invention provides the option to have a tested vaccine against FMD available, keeping its potency for an extended time when compared to the present situation wherein tested FMD vaccine is stored at 4° C.

The present invention also pertains to method for testing an immunogenic composition for administration to an animal, said composition comprising an antigen and an emulsion which is a single emulsion at a first temperature below a body temperature of the animal and which emulsion reverses at a second temperature between the first temperature and the body temperature, said method comprising formulating the immunogenic composition, freezing the composition, storing the frozen composition for a predetermined time, thawing the composition, and determining the potency of the thawed composition.

The present invention also pertains to a combination of an immunogenic composition for administration to an animal, said composition comprising an antigen and an emulsion which is a single emulsion at a first temperature below a body temperature of the animal and which emulsion reverses at a second temperature between the first temperature and the body temperature, and an instruction that the composition may be stored at a temperature below a freezing temperature of this composition until needed for administration to the animal. In an embodiment the combination is a package (for example a box, vial, flask or any other container) comprising the composition and the instruction in tangible form (for example in the form of a leaflet, printed instructions on the package or in the form of a sticker glued to the package). In an alternative embodiment the combination is a recommendation made public via oral or written description, for example the recommendation that immunogenic composition "X" may be frozen and stored in that condition until needed for administration. The recommendation might for example be shown on a web-site of a distributor or manufacturer of a particular immunogenic composition, or is made public via an article in a journal, presentation on a congress or other equivalent happing, or is presented, either solely via oral means or in written form or a combination of oral and written form, in a commercial presentation such as a television-commercial or a presentation in a booth of a medical or scientific gathering.

The invention also pertains to a liquid immunogenic composition for administration to an animal, the composition comprising an antigen and an emulsion which is a single emulsion at a first temperature below a body temperature of the animal and which emulsion reverses at a second temperature between the first temperature and the body temperature, which composition was frozen around −20° C. and thawed thereafter to become liquid.

EXAMPLES OF THE INVENTION

Example 1, in conjunction with FIGS. 1, 2 and 3, shows the effect of freezing on the emulsion quality of various emulsions.

Example 2 describes the effect of various types of freezing on the macroscopic consistency of an emulsion.

Example 3 shows the effect of storing on the potency of an immunogenic composition adjuvanted with an oil-in-water emulsion.

Example 1

In this example the effect of freezing on the emulsion quality of various commercially available emulsions is shown. For this we used the emulsions of the following FMD vaccines: CEDIVAC®-FMD (available from Central Institute for Animal Diseases Control, Lelystad, The Netherlands), AFTOVACIN® OLEOSA (available from Intervet/Schering-Plough Animal Health, Moinho Velho, Brasil) and DECIVAC® FMD DOE (available from Intervet/Schering- Plough Animal Health, Boxmeer, The Netherlands). The emulsion quality is assessed microscopically. Each emulsion is viewed as is, that is when stored at 4° C., and after the emulsion has been frozen in a regular compressor-type household freezer at −20° C., stored for 5 consecutive days in this freezer, thawed and warmed to 4° C.

Figure 1A:
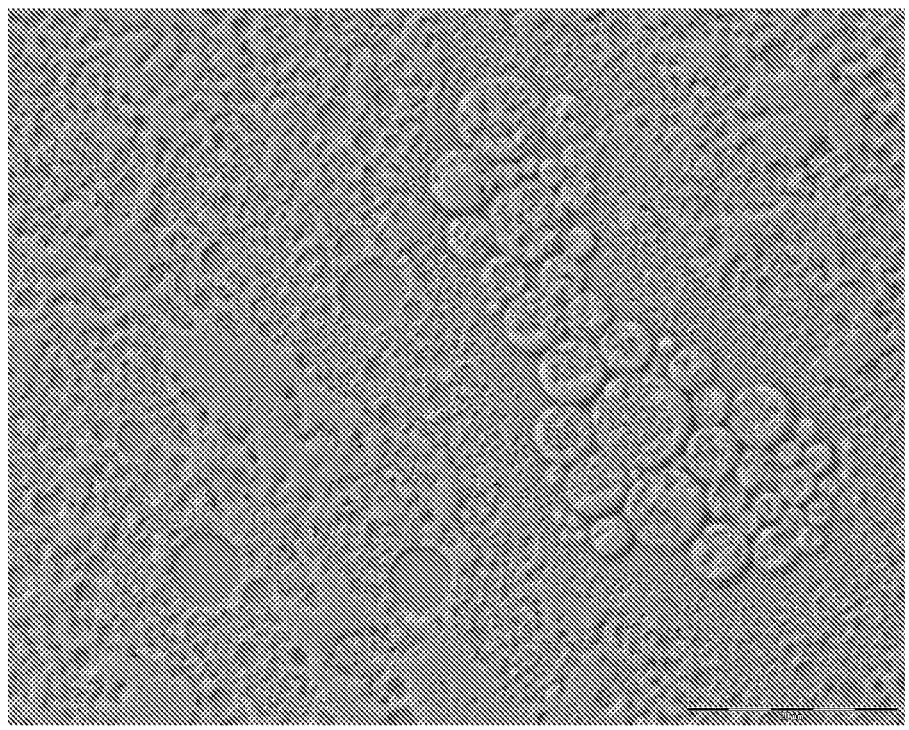
FIG. 1A shows the CEDIVAC®-FMD emulsion after regular storing at 4° C.
Figure 1B:
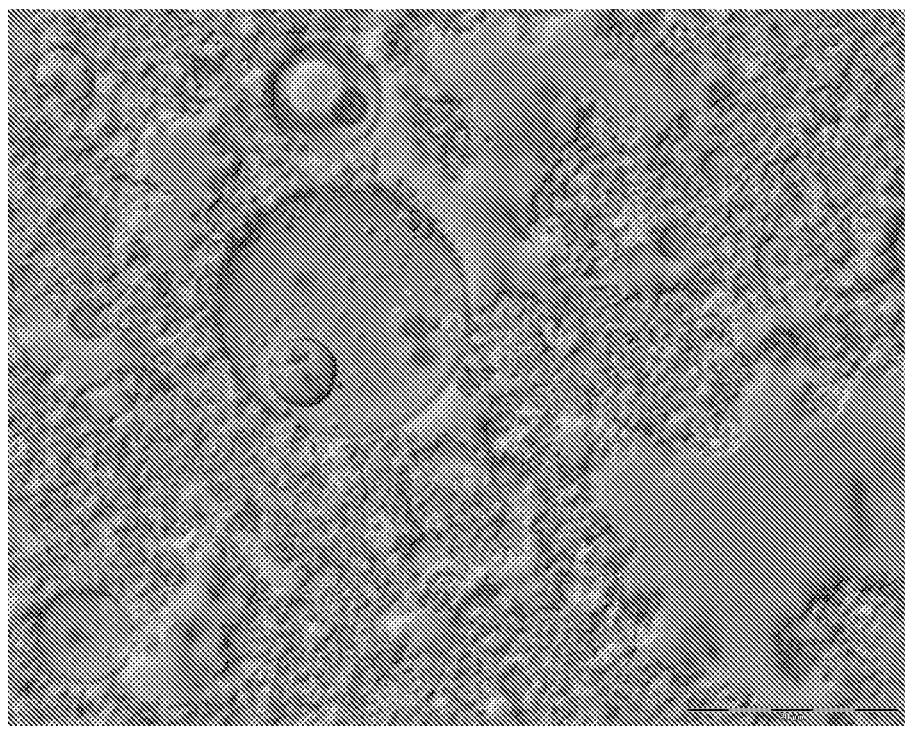
FIG. 1B shows a corresponding picture of the emulsion of FIG. 1A, but when stored in frozen condition.

The results are shown in FIGS. 1, 2 and 3. FIG. 1A shows the CEDIVAC®-FMD emulsion after regular storing (corresponding to supplier's instructions) at 4° C. It can be seen that the emulsion is a double emulsion (in this case of the water-in-oil-in-water type). FIG. 1B shows a corresponding picture of this emulsion when stored in frozen condition as indicated here-above. It is clear that the emulsion quality is dramatically influenced. A lot of coagulation has apparently taken place.

Figure 2A:
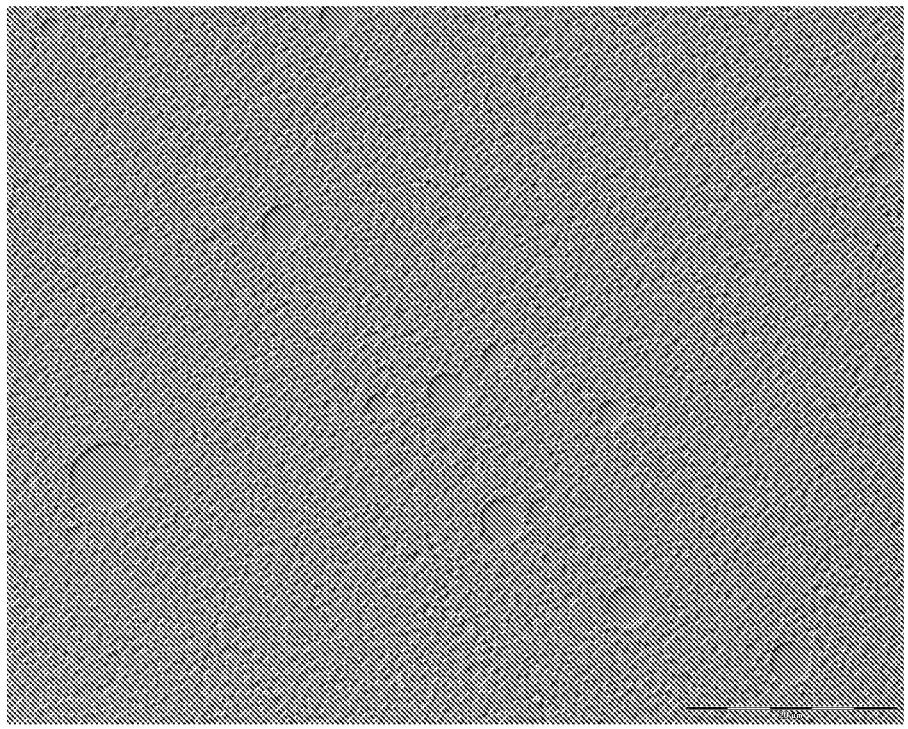
FIG. 2A shows the AFTOVACIN® OLEOSA emulsion after regular storing at 4° C.
Figure 2B:
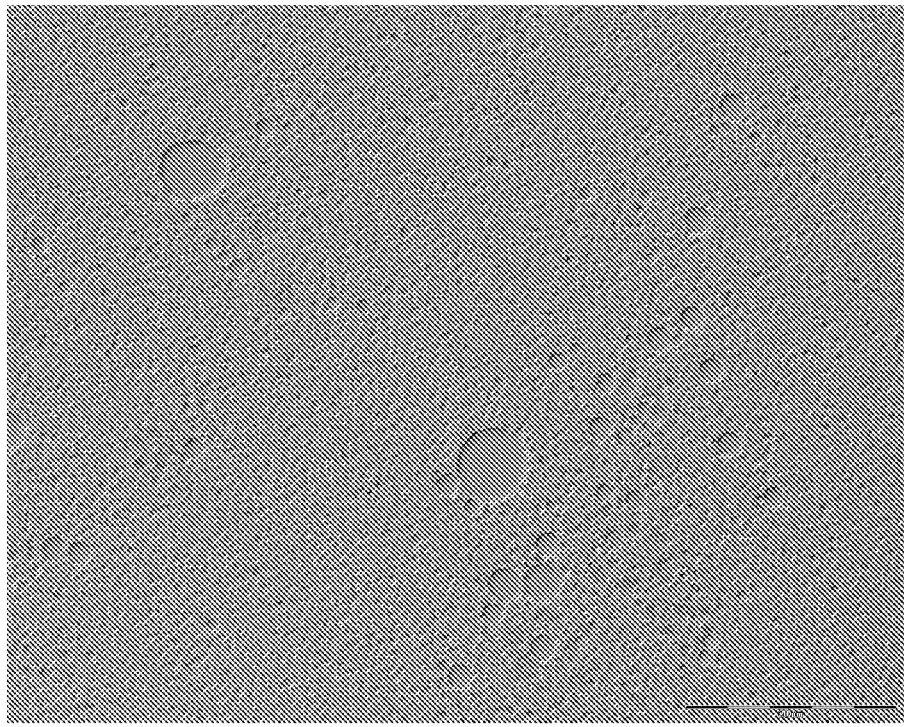
FIG. 2B shows a corresponding picture of the emulsion of FIG. 2A, but when stored in frozen condition.

FIG. 2A shows the AFTOVACIN® OLEOSA emulsion after regular storing (corresponding to supplier's instructions) at 4° C. It can be seen that the emulsion is a single emulsion (in this case of the water-in-oil type). FIG. 2B shows a corresponding picture of this emulsion when stored in frozen condition as indicated here-above. It is clear that the emulsion quality is hardly influenced.

Figure 3A:
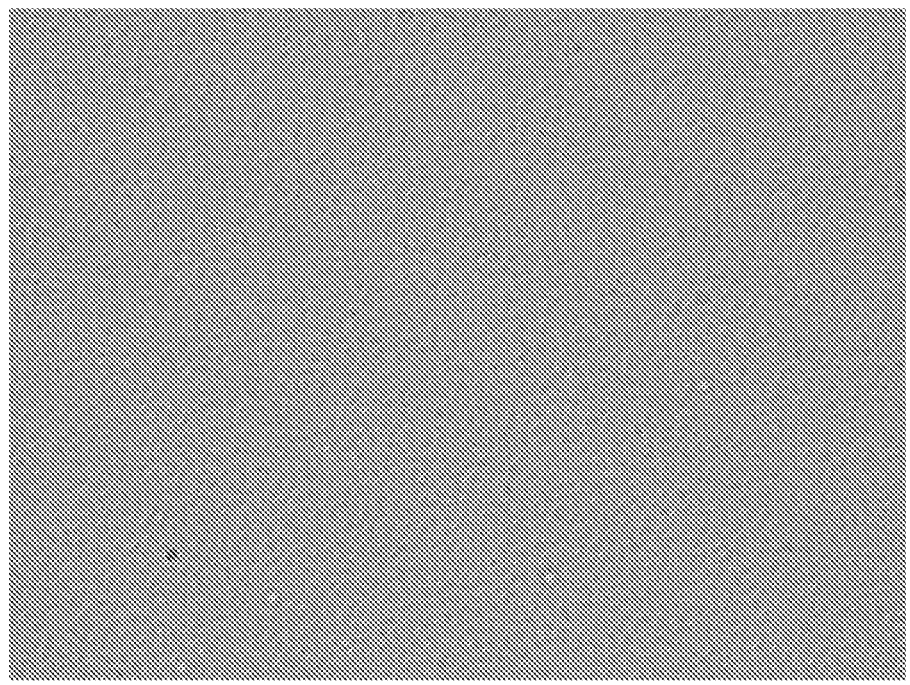
FIG. 3A shows the DECIVAC® FMD DOE emulsion after regular storing at 4° C.
Figure 3B:
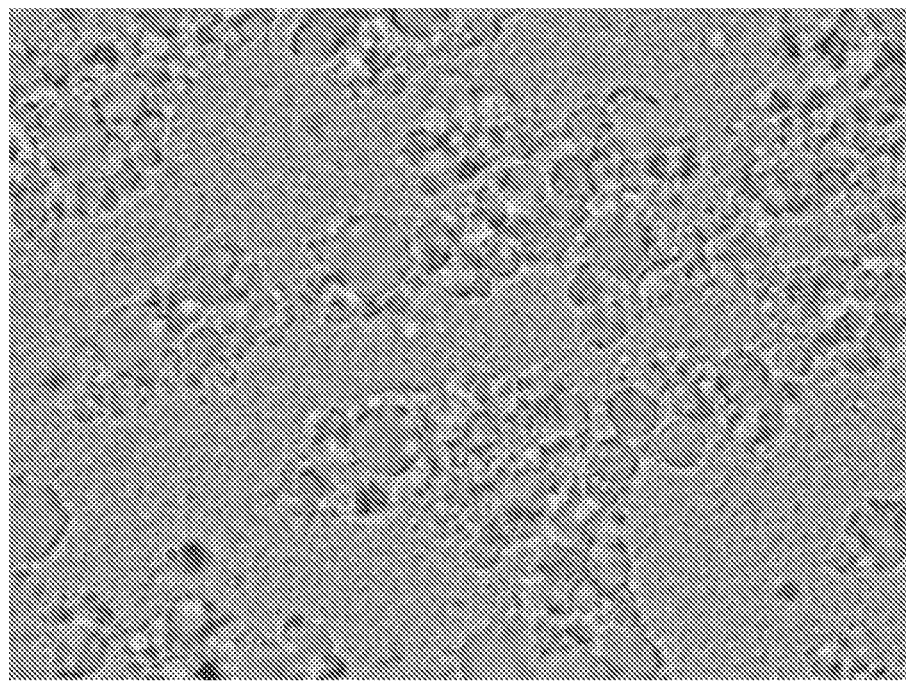
FIG. 3B shows a corresponding picture of the emulsion of FIG. 3A, but when stored in frozen condition.

FIG. 3A shows the DECIVAC® FMD DOE emulsion after regular storing (corresponding to supplier's instructions) at 4° C. The emulsion is a single emulsion of the oil-in-water type (wherein the oil comprises a mixture of mannide oleate and mineral oil, commercially available as MONTANIDE® ISA 206, from SEPPIC, Paris, France), but reverses to a water-in-oil type when heated to 37° C. FIG. 3B shows a corresponding picture of this emulsion when stored in frozen condition as indicated here-above. It is clear that the emulsion quality is dramatically influenced. A lot of coagulation has apparently taken place.

These results indicate that the emulsion of the type as present in the commercially available vaccine DECIVAC® FMD DOE is prone to a dramatic loss in emulsion quality when the emulsion is frozen, in particular in the non snap-freezing process as used in this example. This is commonly believed to correspond to a significant loss in adjuvanting properties.

Example 2

In this example the effect of various types of freezing on the macroscopic consistency of a single emulsion is described. In this case the experiment was performed with the emulsion of the commercially available DECIVAC® FMD DOE vaccine. One sample of the emulsion was snap-frozen by putting a glass vial containing the emulsion in liquid nitrogen en keeping it there for 24 hours. A second sample of the emulsion was subjected to a non snap-freezing process by putting a vial containing the emulsion in a standard house-hold freezer, having an inner temperature of −20° C., and keeping the vial in the freezer for 24 hours. After that, both samples were thawed by subjecting the vials to ambient conditions (normal air, 21° C., atmospheric pressure). Thereafter, the emulsion quality was macroscopically assessed by subjecting the vials to visual inspection. It appeared that the emulsion subjected to non snap-freezing showed significantly more coagulation of the oil-phase. From this, it may be concluded that non snap-freezing has a greater influence on emulsion quality for this type of emulsion than snap-freezing.

Example 3

In this example the effect of storing on the potency of an immunogenic composition adjuvanted with an oil-in-water emulsion is shown. In this example a worse case scenario is chosen, namely an immunogenic composition having therein three FMD antigens, which are known to be notoriously unstable. Therefore, the effect that storing has on the potency of the composition can be recognised within a time-frame of months. For stable antigens, this could take up to several years. The principles however remain the same: to show what the (non) effect is of freezing on the adjuvanting properties of the emulsion used in the present invention.

For the experiment we used a DECIVAC® FMD DOE vaccine, in this case containing the antigens O1 Manisa, A22 Iraq and Asia 1 Shamir. Samples of the vaccine were either stored at 4° C. ("Liquid") or frozen in a standard freezer at about −20° C. ("Frozen") and stored in that freezer. The potency of the stored vaccines is determined (after 4 and 12 months storage) by vaccinating 5 animals (cattle) with a single dose (2 ml) and bleeding the cattle after 28 days. Serum is prepared from the blood. The neutralizing antibody titer against FMD virus of homologous serotype is determined in the serum sample per animal. The mean titer corresponds to the potency of the vaccine. The results are shown here-beneath in FIGS. 4, 5 and 6.

Figures 4, 5:
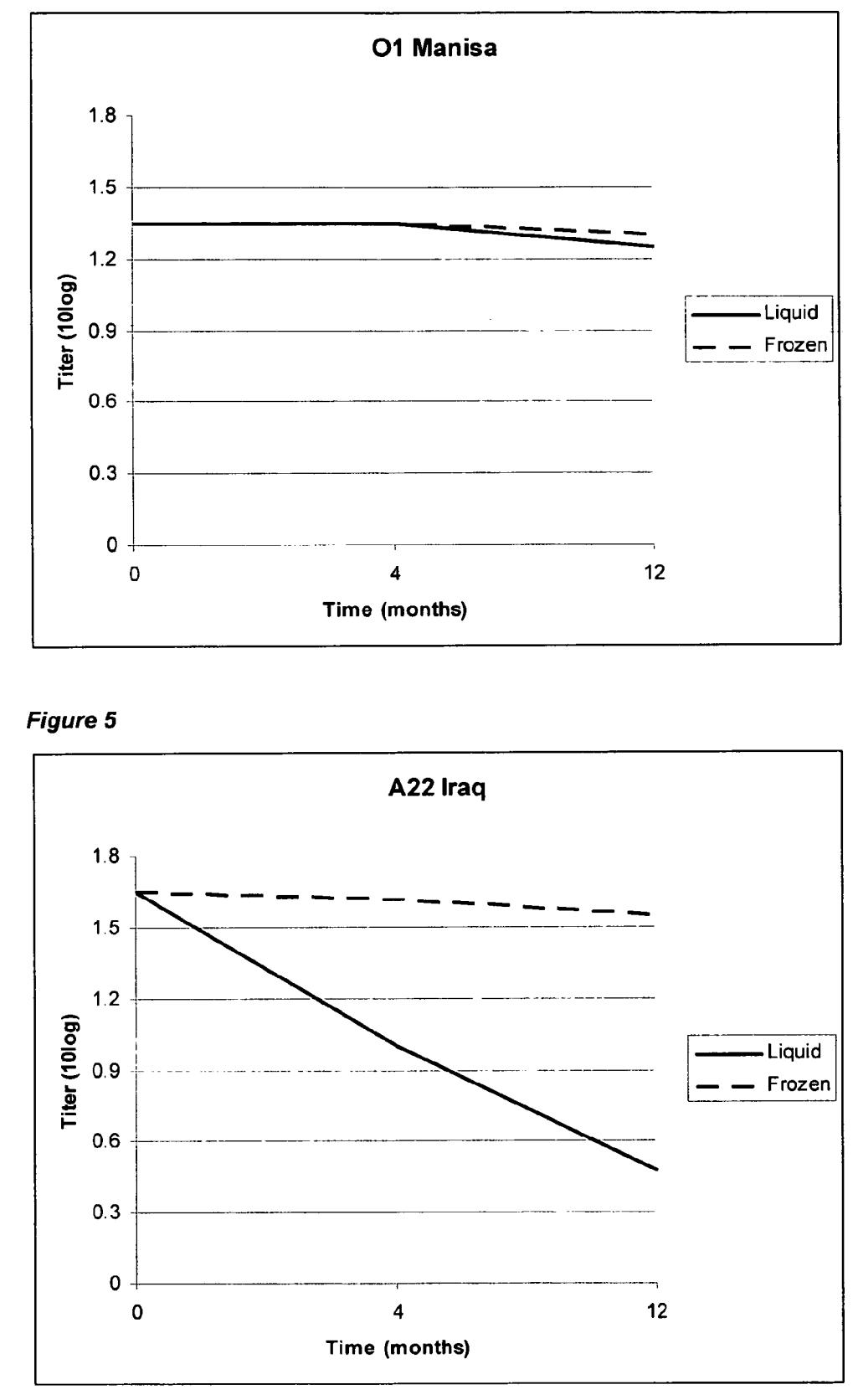

From FIG. 4 it appears that the O1 Manisa antigen is relatively stable in the observed time period. Still, it can be seen that the potency of the frozen vaccine after 12 months of storage is somewhat better than that of the vaccine stored at 4° C. Therefore, the adjuvanting properties of the frozen emulsion are still adequate.

For the A22 Iraq antigen it becomes clear that storage at 4° C. is detrimental for the potency. Apparently, the antigen itself loses its immunogenic properties, and not the adjuvant emulsion, since the emulsion on itself remains stable for at least about 5 years when stored at 4° C. When stored at −20° C., the potency decreases hardly. Apparently, the antigen is quite stable at −20° C. Also, the emulsion apparently keeps its immunogenic properties when it is stored in frozen condition.

For the third antigen, Asia 1 Shamir, one can see a situation corresponding to that with the A22 Iraq antigen. Given the fact that for the vaccine kept in frozen condition the potency remains unaltered during storage, it must be concluded that the adjuvanting properties of the emulsion have not been negatively influenced at all by the freezing process and storage.

In short, from these experiments it may be concluded that the adjuvanting properties of the emulsion remain completely intact when the emulsion as defined in the appended claims, or a vaccine based on this emulsion, is frozen. In particular, a non snap-freezing process, although being detrimental for the emulsion quality, appears to suffice, even when using a freezing temperature as high as about −20° C. The advantages of this invention can be used for increasing the shelf-life of any immunogenic composition which is based on an emulsion as adjuvant.

The invention claimed is:

1. A method for keeping a killed foot-and-mouth disease vaccine available for emergency vaccination of animals against foot-and-mouth disease, the vaccine comprising a foot-and-mouth disease antigen formulated in a water-in-oil emulsion, said method comprising: providing the formulated vaccine, freezing the vaccine, and storing the frozen vaccine until it is needed for emergency vaccination; wherein the vaccine is frozen by using a non-snap-freezing process; and wherein the method has no or hardly any negative influence on the potency of the vaccine.

2. The method of claim 1, wherein a potency of the vaccine is established before it is stored.

3. The method of claim 1, wherein prior to the step of freezing the vaccine, the vaccine is supplied to a party.

4. The method of claim 1, wherein the vaccine is supplied to a party after it has been frozen.

5. The method of claim 1, wherein the vaccine is frozen in a compressor type freezer.

6. The method of claim 1, wherein the freezing process takes place at around −20° C.

7. The method of claim 1, wherein the water-in-oil emulsion is based on mineral oil.

8. A method for testing a killed foot-and-mouth disease vaccine comprising a foot-and-mouth disease antigen formulated in a water-in-oil emulsion, said method comprising: formulating the vaccine, freezing the vaccine, storing the frozen vaccine for a predetermined time, thawing the vaccine, and determining the potency of the thawed vaccine; wherein the vaccine is frozen by using a non-snap-freezing process.

9. The method of claim 6, wherein the water-in-oil emulsion is based on mineral oil.

* * * * *